United States Patent [19]

Timko

[11] 4,383,947

[45] May 17, 1983

[54] INTRODUCTION OF A FLUORINE ATOM

[75] Inventor: Joseph M. Timko, Kalamazoo, Mich.

[73] Assignee: The Upjohn Company, Kalamazoo, Mich.

[21] Appl. No.: 286,306

[22] Filed: Jul. 24, 1981

[51] Int. Cl.$^3$ .................................................. C07J 1/00
[52] U.S. Cl. ............................... 260/397.45; 260/397.3
[58] Field of Search ........................... 260/397.3, 397.45

[56] References Cited

U.S. PATENT DOCUMENTS

| | | | |
|---|---|---|---|
| 2,961,441 | 11/1960 | Bogert et al. | 260/239.55 |
| 3,014,938 | 12/1961 | Mills et al. | 260/397.47 |
| 3,126,375 | 3/1964 | Ringold et al. | 260/239.55 |
| 3,127,428 | 3/1964 | Tanabe et al. | 260/397.4 |
| 3,178,412 | 4/1965 | Ringold | 260/239.55 |
| 3,221,033 | 11/1965 | Shapiro | 260/397.4 |
| 3,332,967 | 7/1967 | Oliveto et al. | 260/397.45 |
| 3,980,778 | 9/1976 | Ayer et al. | 424/243 |
| 4,041,055 | 8/1977 | Shephard et al. | 260/397.3 |
| 4,127,596 | 11/1978 | Beaton et al. | 260/397.3 |
| 4,188,322 | 2/1980 | Castelli et al. | 260/239.55 |
| 4,232,015 | 11/1980 | Teutsch et al. | 260/397.45 |

OTHER PUBLICATIONS

J. Am. Chem. Soc. 82, 4001 (1960).
Steroids, Fieser and Fieser, Reinhold Pub., New York, 1959, p. 685.
Steroid Reactions, C. Djerasi, Hogan-Day, 1953, Chapter 3, p. 155.

*Primary Examiner*—Elbert L. Roberts
*Attorney, Agent, or Firm*—Bruce Stein

[57] ABSTRACT

Perchloryl fluoride when reacted with the appropriately protected 9α-hydroxyandrostenedione stereoselectively produces the corresponding 6β-fluoro steroid.

14 Claims, No Drawings

INTRODUCTION OF A FLUORINE ATOM

BACKGROUND OF THE INVENTION

Steroids with a fluorine atom at the six position in the α configuration are known to increase the anti-inflammatory activity over the corresponding steroid without a fluorine atom at the six position. Numerous anti-inflammatory agents are known containing a 6α-fluoro atom. In the $\Delta^{1,4}$-3-keto series, diflorasone diacetate, fluocortolone, fluocinolone acetonide, fluocinonide, paramethasone, fluprednisolone, and flumethasone all contain a 6α-fluoro group, and in the $\Delta^4$-3-keto series flurandrenolide has a 6α-fluorine atom.

Until U.S. Pat. No. 4,188,322 issued in 1980, previous technology required that the production of the 6α-fluoro-$\Delta^{1,4}$-3-keto steroids necessitated the introduction of a fluorine atom at the 6β-position followed by the epimerization of the 6β-fluoro atom of the steroid prior to $\Delta^1$-dehydrogenation. See for example U.S. Pat. Nos. 3,980,778, 3,014,938 and 3,126,375 and J. Am. Chem. Soc. 82, 4001 (1960).

Various methods are known for the introduction of a fluorine atom at the six position in a steroid. See, for example, Steroids, Fieser and Fieser, Reinhold Publishing Co., N.Y., 1959, p. 685; and Steroid Reactions, Carl Djerassi, Hogan-Day, Inc., San Francisco, 1953, Chapter 3, p. 155.

More particularly, perchloryl fluoride is well known for introduction of a fluorine atom into the six position of a steroid, including reactions with both enol ethers and enol acetates. However, the reaction of perchloryl fluoride with 9α-hydroxy steroids has not been reported.

When perchloryl fluoride has been used to introduce a fluorine atom at the six position of steroidal enol ethers or enol acetates, both the 6α-fluoro and 6β-fluoro isomers are produced, giving a mixture. U.S. Pat. Nos. 2,961,441 and 3,178,412 disclose the reaction of perchloryl fluoride and a number of steroids and refers to the production of 6β-fluoro steroids. Example 1 of U.S. Pat. No. 2,961,441 discloses a 79% yield of the 6β product. The majority of the remaining 21% is the 6α-fluoro isomer. The process of U.S. Pat. No. 3,178,412 also produces a mixture of 6α and 6β isomers; see, for example, where it states that the 6β-isomer predominates (Example IV) and that the 6β and 6α compounds were obtained (Example X). It has been discovered that when the steroidal substrate is a 9α-hydroxy steroid, the resulting 6-fluoro product is not a mixture of 6α- and 6β-fluoro isomers, but only a 6β-fluoro steroid.

BRIEF DESCRIPTION OF THE INVENTION

Disclosed is a process for producing a 6β-fluoro-9α-hydroxyandrost-4-ene-3,17-dione (III) which comprises (1) contacting a $C_3$-protected 3,9α-dihydroxyandrosta-3,5-dien-17-one (II) with perchloryl fluoride ($FClO_3$) and (2) isolating the desired 6β-fluoro-9α-hydroxyandrost-4-ene-3,17-dione.

Further disclosed are the $C_3$-protected 3,9α-dihydroxyandrosta-3,5-dien-17-one (II), the 6β-fluoro-9α-hydroxyandrost-4-ene-3,17-dione (III), 6β-fluoroandrost-4,9(11)-diene-3,17-dione (IV), 6α-fluorovandrost-4,9(11)-diene-3,17-dione (V), 17α-ethynyl-6-fluoro-17β-hydroxyandrosta-5,9(11)-dien-3-one (VI) and 17α-ethynyl-6α-fluoro-17β-hydroxyandrosta-4,9(11)-dien-3-one (VII).

DETAILED DESCRIPTION OF THE INVENTION

The process of the present invention introduces a fluorine atom into a $C_3$-protected 3,9α-dihydroxyandrosta-3,5-dien-17-one (II) at the $C_6$ position surprisingly and unexpectedly solely in the β-configuration.

Chart A discloses the process of the present invention as well as a number of novel intermediates. The 9α-hydrosyandrostenedione (I) starting materials are well known to those skilled in the art or can readily be prepared from compounds well known to those skilled in the art by processes well known to those skilled in the art. See, for example, U.S. Pat. Nos. 3,065,146, 4,035,236, 3,391,169 and 3,704,253. The 9α-hydroxyandrostenedione (I) starting material is either a $\Delta^4$-3-keto steroid ($\cdots\cdots\cdots$ is a single bond) or a $\Delta^{1,4}$-3-keto steroid ($\cdots\cdots\cdots$ is a double bond). It is preferred that the 9α-hydroxyandrostenedione (I) starting material be a $\Delta^4$-3-keto steroid. In addition, $C_{16}$ can be substituted with a methyl group ($R_{16}$ is methyl) in either the α or β configuration. It is preferred that $R_{16}$ is a hydrogen atom and there be no methyl group at $C_{16}$.

The 9α-hydroxyandrostenedione (I) starting material has the ketone at $C_3$ with must be protected as an enol ether or enol acylate, by methods very well known to those skilled in the art. It is preferred that the $C_3$ protecting group is the acylate and it be the acetate ester. When the $C_3$ enol acylate is formed, the 9α-hydroxy group may also be acylated. If this occurs, no problem results and the 3,9-diacylate can be fluorinated by the process of the present invention in the same way as the $C_3$-protected 3,9α-dihydroxyandrost-3,5-dien-17-one (II). The $C_3$-protected 3,9α-dihydroxyandrosta-3,5-dien-17-one (II) is reacted with perchloryl fluoride ($FClO_3$), by means well known to those skilled in the art for introduction of a fluorine atom at the $C_6$ position of a steroid, to give the corresponding 6β-fluoro-9α-hydroxyandrost-4-ene-3,17-dione (III). See, for example, J. Am. Chem. Soc. 81, 5259 (1959), Chem. and Ind. 2050 (1961), Ibid., 1317 (1959), and U.S. Pat. Nos. 2,961,441 and 3,178,412. The reaction can be performed in the presence of most any solvent in which the $C_3$-protected 3,9α-dihydroxyandrosta-3,5-dien-17-one (II) is soluble. Polar organic solvents are preferred, especially substituted formamides, THF, methanol, ethanol and mixtures thereof. DMF is the preferred solvent. The reaction works best without any water present. However, water is added to reduce the explosive potential of the organic solvent vapor; the more water in the reaction mixture, the less chance for an explosion, but the poorer the reaction performs. Water (0–50%) is workable; preferably, 5–40% is used; more preferably, 10–30% water is used. The reaction is operable in a temperature range of −20° to 100°, preferably 20°–50°, using a nitrogen atmosphere. A soluble lead compound such as lead subacetate is added to reduce the chlorination of the $C_3$-protected 3,9α-dihydroxyandrosta-3,5-dien-17-one (II). The perchloryl fluoride is bubbled through the mixture of the $C_3$-protected 3,9α-dihydroxyandrosta-3,5-dien-17-one (II) in the polar organic solvent and water. When the reaction is complete, 1–5 hr, as monitored by TLC, nitrogen is sparged in to remove the excess perchloryl fluoride, and the 6β-fluoro-9α-hydroxyandrost-4-ene-3,17-dione (III) is recovered by means well known to those skilled in the art.

The 6β-fluoro-9α-hydroxyandrost-4-ene-3,17-dione (III) is then converted to the corresponding 6β-fluoroandrost-4,9(11)-diene-3,17-dione (IV) by any of a number of known processes. See, for example, U.S. Pat. Nos. 4,102,596 and 4,127,596. In the present case (Examples 3 and 9), chlorosulfonic acid was used for the dehydration of the 9α-hydroxy group to the $\Delta^{9(11)}$ functionality.

The 6β-fluorine atom of the 6β-fluoroandrost-4,9(11)-diene-3,17-dione (IV) is then isomerized to a 6α-fluorine atom, by means well known to those skilled in the art, producing the corresponding 6α-fluoroandrost-4,9(11)-diene-3,17-dione (V). See, for example, Chem. and Ind. 2050 (1961), Chem. and Ind. 1317 (1959), Tetrahedron 3, 14 (1958), and U.S. Pat. No. 3,178,412. In the present case (Examples 4 and 10), dry hydrogen chloride is used for the isomerization.

The 6α-fluoroandrost-4,9(11)-diene-3,17-dione (V), is then converted to a 6-fluoroethisterone type compound, 17α-ethynyl-6-fluoro-17β-hydroxyandrost-5,9(11)-dien-3-one (VI), by means well known to those skilled in the art for the addition of acetylene to a 17-keto steroid to form the well known 17α-ethynyl-17β-hydroxy functionality. See, for example, Steroids, Fieser and Fieser, Reinhold Publishing Co., New York, 1959, p. 557, and U.S. Pat. No. 4,041,055.

Last, the 5,6-double bond is isomerized to the desired 4,5-position with the fluorine atom at the C₆ position, obtaining the desired αconfiguration. This isomerization procedure is well known to those skilled in the art utilizing an acid such as p-TSA or hydrochloric acid. Hence, the 17α-ethynyl-6-fluoro-17β-hydroxyandrost-5,9(11)-diene-3-one (VI) is converted to the desired corresponding 17α-ethynyl-6α-fluoro-17β-hydroxyandrost-4,9(11)-dien-3-one (VII).

Alternatively, Chart C discloses that the desired 6α-fluoroandrost-4,9(11)-diene-3,17-dione (V) intermediate can be obtained by starting with a $\Delta^{9(11)}$ steroid such as androsta-4,9(11)-diene-3,17-dione (VIII) rather than a 9α-hydroxy steroid such as 9α-hydroxyandrost-4-ene-3,17-dione (I). If one starts with an androsta-4,9(11)-diene-3,17-dione (VIII), a very similar procedure is followed, see Chart C, (1) protect the steroid at C₃, (2) fluorinate at C₆ with perchloryl fluoride, and (3) isomerize the 6β-fluorine atom to the 6α configuration. The 6α-fluoroandrosta-4,9(11)-diene-3,17-dione (V) intermediate is then transformed to the corresponding 6α-fluoro ethisterone (VII) as previously described.

The 6α-fluoroethisterones (VII) are useful intermediates in the synthesis of pharmacologically active corticoids and 17α-hydroxyprogesterones, see U.S. Pat. No. 4,041,055.

DEFINITIONS

The definitions and explanations below are for the terms as used throughout the entire patent application, including both the specification and claims.

All temperatures are in degrees Centigrade.
TLC refers to thin-layer chromatography.
THF refers to tetrahydrofuran.
DMF refers to dimethylformamide.
p-TSA refers to p-toluenesulfonic acid.
NMR refers to nuclear (proton) magnetic resonance spectroscopy, chemical shifts are reported in ppm (δ) downfield from TMS.

When solvent pairs are used, the ratio of solvents used is volume/volume (v/v).

$R_3$ is alkyl of 1 thru 3 carbon atoms or $R_3'$—CO—.

$R_3'$ is alkyl of 1 thru 3 carbon atoms or phenyl.

$R_{16}$ is a hydrogen atom or methyl group.

~ indicates the attached group can be in the α or β configuration.

........... is a single or double bond.

When the term "alkyl of __ thru __ carbon atoms" is used, it means and includes isomers thereof where such exist.

Perchloryl fluoride refers to $FClO_3$.

Androstenedione refers to androst-4-ene-3,17-dione.

Ethisterone refers to 17α-ethynyl-17β-hydroxyandrost-4-ene-3-one.

Lead subacetate refers to $Pb(OCOCH_3)_2.2\ Pb(OH)_2$.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

3,9α-Dihydroxyandrost-3,5-diene-17-one 3-enol acetate (II)

Acetic anhydride (30 ml) and acetyl chloride (36 ml) are added to THF (60 ml) containing 9α-hydroxyandrostenedione (I, 10.0 g). The mixture is heated at 55° for 3.5 hours and then cooled. The THF is removed under reduced pressure and the resulting solution poured into water. The solid is recovered by filtration and taken up in ethyl acetate (100 ml). The ethyl acetate mixture is washed with water and then dried over sodium sulfate and then the ethyl acetate removed under reduced pressure to give a solid. Crystallization from ethyl acetate-hexane gives the title compound. Rf=0.5 (ethyl acetate-hexane, 1/1); NMR (CDCl₃) 0.9, 1.2, 2.1, 5.5 and 5.7 δ.

EXAMPLE 2

6β-fluoro-9α-hydroxyandrost-4-ene-3,17-dione (III)

Water (35 ml, nitrogen purged) containing sodium acetate (700 mg) and lead sub-acetate (1.05 g) is added to DMF (105 ml, purged with nitrogen) containing 3,9α-dihydroxyandrost-3,5-diene-17-one-3-enol acetate (II, Example 1, 7.0 g) previously cooled to 5°. The mixture is warmed to 40° and FClO₃ is slowly sparged in. A large reservoir is placed between the reaction vessel and the FClO₃ tank in order to prevent a potentially disastrous backflow of reaction mixture into the tank. After 3.5 hrs the heating is discontinued and nitrogen is sparged in for 20 min to remove excess perchloryl fluoride. The mixture is cooled to 5° and cold water (150 ml) added. The mixture is stirred for 10 min, filtered, and the filtrate washed with water. The filter cake is slurried in methylene chloride (150 ml), sodium sulfate added and the mixture filtered through Celite to remove the lead solid to give the title compound in solution. The diluent is removed to obtain the title compound as a solid. The aqueous washes are back extracted with ethyl acetate which is extensively washed with water to remove DMF. The ethyl acetate mixture is dried over sodium sulfate, filtered, and the ethyl acetate removed under reduced pressure to give a solid. The solid is crystallized from methylene chloride/methanol/ethyl acetate to give additional title compound.

$R_f=0.3$ (ethyl acetate-hexane, 1/1); NMR ($CDCl_3+CD_3OC+DMSO-d_6$) 0.9, 1.4, 5.0 and 5.9 δ.

EXAMPLE 3

6β-Fluoroandrost-4,9(11)-diene-3,17-dione (IV)

Chlorosulfonic acid (2.0 ml) is added to methylene chloride (50 ml) containing 6β-fluoro-9α-hydroxyandrost-4-ene-3,17-dione (III, Example 2, 5.2 g) previously cooled to −20°. After 1.25 hr, the cold solution is quenched by adding slowly water (2 ml). The organic mixture is then washed with water, aqueous sodium carbonate, dried over sodium sulfate, and the organic solvent removed under reduced pressure to give the title compound. $R_f$ (ethyl acetate/hexane, 1/1)=0.5; NMR ($CDCl_3$) 0.9, 1.5, 5.1, 5.6 and 5.9 δ.

EXAMPLE 4

6α-Fluoroandrost-4,9(11)-diene-3,17-dione (V)

Dry hydrochloric acid gas is bubbled for 30 seconds into DMF (10 ml) containing 6β-fluoroandrost-4,9(11)-diene-3,17-dione (IV, Example 3, 650 mg). After two days, water is added, the acid neutralized with aqueous sodium bicarbonate, and the product filtered to give the title compound. $R_f$ (ethyl acetate/hexane, 1/1)=0.45; NMR ($CDCl_3+CD_3OD$) 0.9, 1.4, 5.1, 5.7 and 6.1 δ.

EXAMPLE 5

17α-Ethynyl-6-fluoro-17β-hydroxyandrost-5,9(11)-diene-3-one (VI)

Potassium t-butoxide (as a 20% solution in THF, 1.6 ml) is added to THF (10 ml) containing 6α-fluoroandrost-4,9(11)-diene-3,17-dione (V, Example 4, 350 mg), previously cooled to −10°. After stirring at −10° for 40 min, acetylene is slowly bubbled in over 2 hrs. The solution is then allowed to warm to 20°–25°, quenched with aqueous ammonium chloride and extracted with ethyl acetate which is then back extracted with water, dried over sodium sulfate, the solvent removed under reduced pressure to give the title compound $R_f$ (ethyl acetate/hexane, 1/1)=0.6; NMR ($CDCl_3+CD_3OD$) 0.9, 1.4, 2.6 and 5.7 δ.

EXAMPLE 6

17α-Ethynyl-6α-fluoro-17β-hydroxyandrost-4,9(11)-diene-3-one (VII)

p-TSA (20 mg) is added to THF (5 ml) containing 17α-ethynyl-6-fluoro-17β-hydroxyandrost-5,9(11)-diene-3-one (VI, Example 5, 200 mg). After one hour at 20°–25°, the mixture is heated to reflux for 1.5 hrs. After cooling, the organic diluent is removed under reduced pressure. The residue is taken up in ethyl acetate, washed with aqueous sodium carbonate, the organic mixtures dried over sodium sulfate, and the organic diluent is removed under reduced pressure to give a solid. Filtration chromatography on silica dioxide (4 g), eluting with methylene chloride with increasing amounts of ethyl acetate, gives the title compound. $R_f$ (ethyl acetate/hexane, 1/1)=0.7; NMR ($CDCl_3+CD_3OD$) 0.8, 1.4, 2.6, 5.3, 5.7 and 6.1 δ.

EXAMPLE 7

3,9α-Dihydroxyandrost-3,5-diene-17-one 3-enol acetate (II)

Acetic anhydride (84 ml) and acetyl chloride (73 ml) is added to ethyl acetate (300 ml) containing 9α-hydroxyandrostenedione (I, 50 g). The resulting suspension is stirred at 30° for 6.25 hrs and cooled in an ice bath for 1.25 hrs. Suction filtration gave a first crop of powdery solid which was washed well with water and dried at 50° under reduced pressure. The mother liquors were concentrated by rotary evaporation to remove the ethyl acetate. The residue was slowly poured into water (2000 ml) with vigorous stirring. Suction filtration gave a solid which was dried at 50° under reduced pressure. The dry solid is then dissolved in methylene chloride, replaced on a rotary evaporator with ethyl acetate and cooled in an ice bath. Suction filtration gave a crop of white solid containing a substantial amount of diacetate impurity.

EXAMPLE 8

6β-Fluoro-9α-hydroxyandrost-4-ene-3,17-dione (III)

A 2 l, 3-necked, round-bottomed flask is equipped with a gas inlet, gas outlet, thermometer and magnetic stir bar. The reaction vessel is flushed with nitrogen and 3,9-dihydroxyandrost-3,5-diene-17-one 3-enol acetate (II, Example 7, 28 g) is added and dissolved in DMF (420 ml previously purged with nitrogen), and the mixture is cooled to 5°. Water (140 ml, previously purged with nitrogen) containing sodium acetate (2.8 g) and lead sub-acetate (4.2 g) is slowly added, keeping the temperature at less than 20°. The resulting solution is warmed to 30° and $FClO_3$ is bubbled in, heating is discontinued after 90 min, and nitrogen is bubbled in for 20 min to remove the excess $FClO_3$. The reaction mixture is cooled to 5° and water (600 ml) is added. After stirring for 10 min., the slurry is filtered and the filter cake is washed well with water. The filter cake is then dissolved in methylene chloride (600 ml) and the organic mixture is dried over sodium sulfate and then filtered through Celite. The Celite cake is then rinsed with methylene chloride. The methylene chloride is removed under reduced pressure with heat to give the title compound. The aqueous washes are extracted twice with ethyl acetate which is then repeatedly washed with water. After drying over sodium sulfate the ethyl acetate mixture is concentrated under reduced pressure with heat to yield additional title compound containing some impurities.

EXAMPLE 9

6β-Fluoroandrost-4,9(11)-diene-3,17-dione (IV)

6β-Fluoro-9α-hydroxyandrost-4-ene-3,17-dione (III, Example 8 21.2 g) is dissolved in methylene chloride (1000 ml) and the mixture dried over magnesium sulfate for 1 hr. After suction filtration (the magnesium sulfate cake is washed with methylene chloride) the filtrate is cooled on an ice bath and chlorosulfonic acid (8.3 ml) is added dropwise keeping the temperature at 0°. The reaction mixture is quenched with water (20 ml) 20 min after the addition of the chlorosulfonic acid is completed. The reaction mixture is transferred to a separatory funnel. The phases are separated. The organic phase is washed repeatedly with water until the pH becomes greater than 5. The organic phase is then dried over sodium sulfate concentrated under reduced pressure to give the title compound.

EXAMPLE 10

6α-Fluoroandrost-4,9(11)-diene-3,17-dione (V)

6β-Fluoroandrost-4,9(11)-diene-3,17-dione (IV, Example 9, 10.5 g) is suspended in acetone (50 ml) and stirred at 20°–25°. Anhydrous hydrochloric acid is bubbled through for approximately one min. After stirring at 20°–25° for 5.5 hr the mixture is cooled in an ice bath and filtered using suction filtration. The solids collected by filtration are rinsed with cold acetone to give the title compound.

EXAMPLE 11

17α-Ethynyl-6-fluoro-17β-hydroxyandrost-5,9(11)-diene-3-one (VI)

Acetylene is bubbled through a mixture of potassium t-butoxide (56.5 ml of a 1.6 M THF solution) in THF (380 ml) for 5 min at 20°–25°. 6α-fluoroandrost-4,9(11)diene-3,17-dione (V, Example 10, 11.8 g) is added portionwise as a solid over several minutes at 20°–25° during which time the acetylene is continually bubbled through the reaction mixture. After 20 min the acetylene addition is stopped and the reaction cooled in an ice bath. Aqueous sulfuric acid (5.6 ml of a mixture of 20 ml of water and 63 g of sulfuric acid) is added slowly while maintaining the temperature less than 15°. Water is added and the THF is removed under reduced pressure. Suction filtration gives a solid which is washed well with water and drying under reduced pressure at 60° gives the title compound.

EXAMPLE 12

17α-Ethynyl-6α-fluoro-17β-hydroxyandrost-4,9(11)-diene-3-one (VII)

17α-Ethynyl-6-fluoro-17β-hydroxyandrost-5,9(11)diene-3-one (VI, Example 11) is dissolved in THF (200 ml) and the mixture dried over sodium sulfate. The dried solution is filtered and cooled in an ice bath to which concentrated hydrochloric acid (20 ml) is added slowly. After stirring at 20°–25° for 3 hr the solution is cooled in an ice bath and water (140 ml) is added followed by sodium hydroxide (50%) to neutralize the solution. The pH is checked by pH meter. The THF is removed under reduced pressure with heat to give a solid which is collected by suction filtration. The solid is washed with water and dried under reduced pressure at 50°. The solid is suspended in ethyl acetate (30 ml) and heated to boiling on a steambath. After stirring for 3 hr at 20°–25° and 2 hr on an ice bath the mixture is filtered using suction and the solids dried under reduced pressure with heat to give the title compound.

EXAMPLE 13

3-Hydroxyandrost-3,5,9(11)-triene-17-one-3-enol acetate (IX)

Isopropenyl acetate (6 ml) and pyridinium p-toluenesulfonate (200 mg) is added to ethyl acetate (25 ml) and androst-4,9(11)-diene-3,17-dione (VIII, 2.84 g). After heating the mixture at reflux for 10 hr, the mixture is cooled and the solvents removed by reduced pressure. The residue is taken up in hot methanol (10 ml) and the product isolated by cooling the mixture to −10°. In a like manner a second crop of crystals is obtained of the title compound. NMR (CDCl₃) 0.9, 1.2, 2.2, 5.5, and 5.76δ.

EXAMPLE 14

6α/6β-Fluoroandrost-4,9(11)-diene-3,17-dione (X)

To DMF (10 ml, previously purged with nitrogen) containing 3-hydroxyandrost-3,5,9(11)-triene-17-one 3-enol acetate (IX, Example 13, 653 mg) cooled to 5° is added water (4 ml), previously purged with nitrogen containing sodium acetate (100 mg) and lead subacetate (150 mg). The mixture is heated to 50° and FClO₃ is slowly sparged in. After 1.5 hr the mixture is cooled, nitrogen sparged in to remove FClO₃ and the mixture cooled to 5°. Water (50 ml) is added and the mixture filtered. The filtrate is taken up in methylene chloride (30 ml) and then filtered through Celite. The organic diluents are evaporated under reduced pressure to give the product as a solid containing a mixture of the 6β-fluoro and 6α-fluoro isomers. NMR (CDCl₃) 0.87, 0.9, 1.4, 1.5, 5.1, 5.4, 5.6, 5.9, and 6.1δ.

EXAMPLE 15

6α-Fluoroandrost-4,9(11)-diene-3,17-dione (V)

Following the general procedures of Examples 4 and 10 and making non-critical variations but starting with 6α/6β-fluoroandrost-4,9(11)-diene-3,17-dione-(X, Example 14) the title compound is obtained.

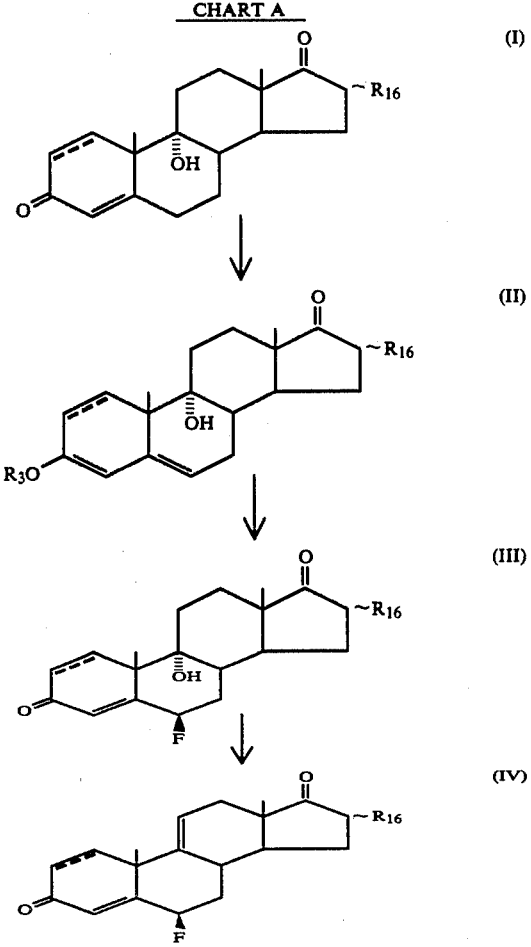

-continued
CHART B

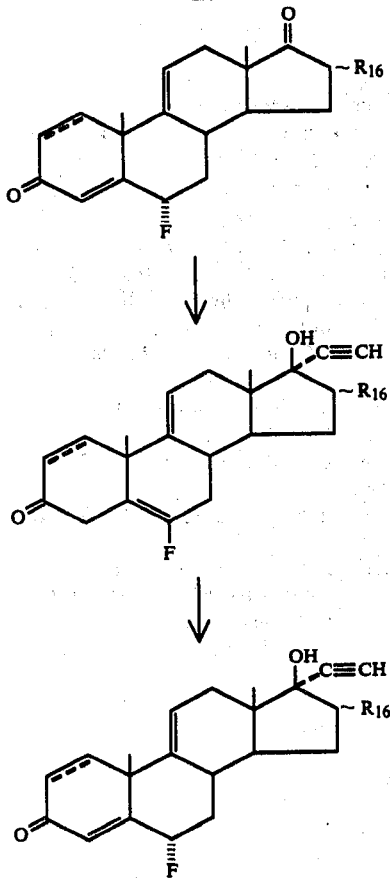

CHART C

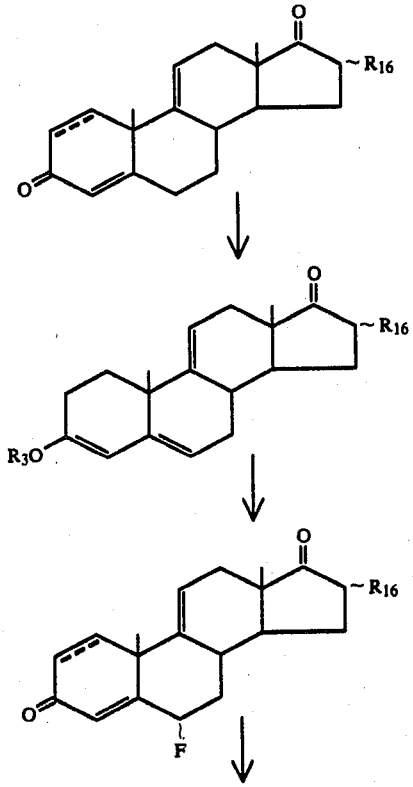

-continued
CHART C

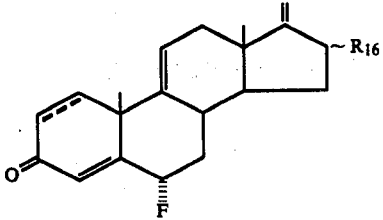

I claim:
1. A C$_3$-protected 3,9α-dihydroxyandrosta-3,5-dien-17-one of the formula

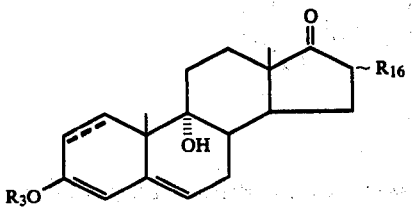

where R$_3$ is alkyl of 1 thru 3 carbon atoms or R$_3'$—CO—, R$_3'$ is alkyl of 1 thru 3 carbon atoms or phenyl, R$_{16}$ is a hydrogen atom or methyl group, ∼ indicates the attached group can be in the α or β configuration, and ---------- is a single or double bond.

2. A C$_3$-protected 3,9α-dihydroxyandrosta-3,5-dien-17-one according to claim 1 wherein R$_{16}$ is a hydrogen atom.

3. A C$_3$-protected 3,9α-dihydroxyandrosta-3,5-dien-17-one according to claim 1 where ---------- is a single bond.

4. A C$_3$-protected 3,9α-dihydroxyandrosta-3,5-dien-17-one according to claim 1 where R$_3$ is acetyl.

5. A C$_3$-protected 3,9α-dihydroxyandrosta-3,5-dien-17-one according to claim 1 which is 3,9α-dihydroxyandrost-3,5-diene-17-one 3-enol acetate.

6. A 17α-ethynyl-6-fluoro-17β-hydroxyandrosta-5,9(11)-dien-3-one of the formula

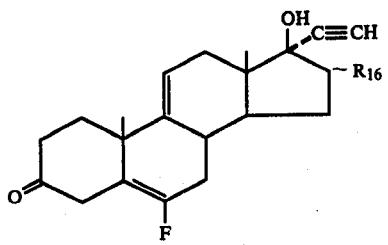

where R$_{16}$ is a hydrogen atom or methyl group, ∼ indicates the attached group can be in the α or β configuration, and ---------- is a single or double bond.

7. A 17α-ethynyl-6-fluoro-17β-hydroxyandrosta-5,9(11)-dien-3-one according to claim 6 wherein R$_{16}$ is a hydrogen atom.

8. A 17α-ethynyl-6-fluoro-17β-hydroxyandrosta-5,9(11)-dien-3-one according to claim 6 where ---------- is a single bond.

9. A 17α-ethynyl-6-fluoro-17β-hydroxyandrosta-5,9(11)-dien-3-one according to claim 6 which is 17α-ethynyl-6-fluoro-17β-hydroxyandrost-5,9(11)-diene-3-one.

10. A process for producing a 6β-fluoro-9α-hydroxyandrost-4-en-3,17-dione of the formula

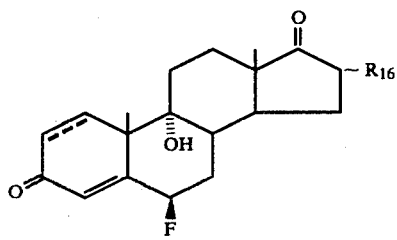

which comprises (1) contacting a C₃-protected 3,9α-dihydroxyandrosta-3,5-dien-17-one of the formula

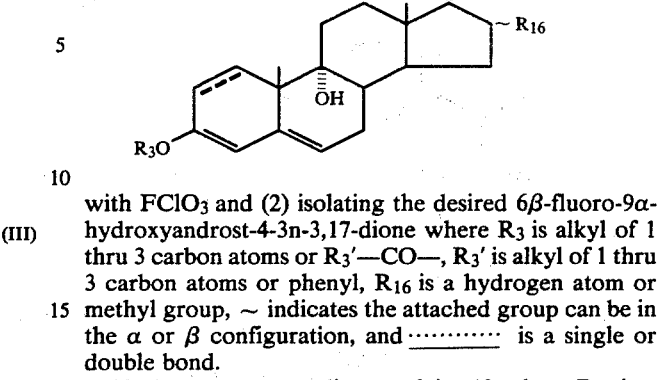

with FClO₃ and (2) isolating the desired 6β-fluoro-9α-hydroxyandrost-4-3n-3,17-dione where R₃ is alkyl of 1 thru 3 carbon atoms or R₃'—CO—, R₃' is alkyl of 1 thru 3 carbon atoms or phenyl, R₁₆ is a hydrogen atom or methyl group, ~ indicates the attached group can be in the α or β configuration, and ············· is a single or double bond.

11. A process according to claim 10 where R₁₆ is a hydrogen atom.

12. A process according to claim 10 where is a single bond.

13. A process according to claim 10 where R₃ is acetyl.

14. A process according to claim 10 where the 6β-fluoro-9α-hydroxyandrost-4-en-3,17-dione is 6β-fluoro-9α-hydroxyandrost-4-ene-3,17-dione.

* * * * *

UNITED STATES PATENT AND TRADEMARK OFFICE
CERTIFICATE OF CORRECTION

PATENT NO. : 4,383,947
DATED : May 17, 1983
INVENTOR(S) : Joseph M. Timko

It is certified that error appears in the above-identified patent and that said Letters Patent is hereby corrected as shown below:

Column 5, line 2, "$CD_3OC +$" should read -- $CD_3OD +$ --.

Column 10, line 63, Claim 8, "where     is a" should read -- where ..... is a --.

Column 12, line 20, Claim 12, "where     is a" should read -- where ..... is a --.

Signed and Sealed this

Seventeenth Day of July 1984

[SEAL]

Attest:

Attesting Officer

GERALD J. MOSSINGHOFF

Commissioner of Patents and Trademarks